United States Patent
Lin

[19]

[11] Patent Number: 5,888,277
[45] Date of Patent: Mar. 30, 1999

[54] AUTOMATIC DISINFECTING MEANS FOR SMOKY GAS IN CONDUIT OR CLOSED SPACE

[75] Inventor: Chien-Hung Lin, Taipei, Taiwan

[73] Assignee: Lacidem International Co., Ltd., Taipei, Taiwan

[21] Appl. No.: 926,041

[22] Filed: Sep. 9, 1997

[51] Int. Cl.[6] ............................................. B01D 47/02
[52] U.S. Cl. .......................... 96/223; 55/312; 55/385.1; 55/417; 55/419; 96/279; 96/351; 422/120; 422/124
[58] Field of Search .................... 15/8, 12, 226, 15/149; 96/223, 226, 227, 329, 351, 267, 278, 279; 55/312, 338, 340, 417, 418, 419, 385.2, 385.1; 422/120, 123, 124, 4

[56] References Cited

U.S. PATENT DOCUMENTS

| | | | |
|---|---|---|---|
| 526,252 | 9/1894 | Moackler | 96/227 |
| 915,000 | 3/1909 | Walter et al. | 96/227 |
| 1,001,094 | 8/1911 | Torchiani | 96/227 |
| 1,814,582 | 7/1931 | Benkert et al. | 96/279 |
| 1,964,794 | 7/1934 | Gilbert | 96/351 |
| 2,262,772 | 11/1941 | Larsen | 422/124 |
| 2,472,011 | 5/1949 | Graham | 422/124 |
| 2,833,528 | 5/1958 | Schroeder | 96/351 |
| 3,576,593 | 4/1971 | Cicirello | 422/124 |
| 3,785,126 | 1/1974 | Smitherman | 96/279 |
| 4,657,566 | 4/1987 | Wintering et al. | 95/226 |
| 5,099,770 | 3/1992 | Yang | 96/278 |
| 5,143,527 | 9/1992 | Tian-Song | 96/351 |
| 5,395,408 | 3/1995 | Zeritis | 96/351 |

*Primary Examiner*—Duane S. Smith
*Attorney, Agent, or Firm*—Bacon & Thomas

[57] ABSTRACT

Smoky gas in conduit or closed space is disinfected by a box body, a blower which is arranged within said box body, an input openings and two output opening which can be switched alternately, a feedback pipe connected to the input opening, a vaporization device and a water collection tank connected to above two output opening, respectively, wherein the vaporization device is extended outside the box body with a circulation pipe and the water collection tank extended outside the box body with a gas outlet pipe; during its operation, feedback pipe and circulation pipe are connected to distal end of conduit or closed space, the disinfecting gas generated by vaporization device is sent to conduit or closed space with the help of blower; after finishing disinfecting work, the gas in feedback pipe is filtered by water collection tank and the purified gas is discharged to atmosphere.

8 Claims, 7 Drawing Sheets

AUTOMATIC DISINFECTING MEANS FOR SMOKY GAS IN CONDUIT OR CLOSED SPACE

BACKGROUND OF THE UTILITY

The present utility relates generally to an automatic disinfecting means for smoky gas in conduit or closed space, more particularly, to a disinfecting means which will disinfect smoky gas in conduit or closed space automatically and the gas released therefrom will not interfere environment and ecology, thus protecting the environment in an improved way.

Conduit and closed space have been found wide application in the field of industry, agriculture, breeding and medical. For examples, conduit may be appeared in the form as chimney, transportation pipe, and closed space in the form as green house, laboratory, reservoir and box for storing wasted. However, they have a common drawback in that inner wall surface and comer thereof are often isolated with outer circumstance and hard to clean such that it is easy to form a hotbed of infect. Therefore, the conduit and closed space need regular clean and disinfecting, especially in the case of medical application where the infect exists extensively and the patient is hard to resist infect.

The present method for disinfecting in a conduit or closed space is to enter thereinto either manually by workmen or by insertion of stick-like tool. However, this kind of disinfecting method is dangerous to workmen as the conduit or closed space is full of infect or cannot eliminate the infect completely as carrying out in a conduit or a narrow closed space.

Moreover, the disinfecting agent or cleaning agent is chemical agent harmful to environment, and manual operation is liable to release those harmful substance to the environment.

SUMMARY OF THE UTILITY

It is an object of the present utility to provide an automatic disinfecting means for smoky gas in conduit or closed space comprising: a box body, a blower which is arranged within the box body and comprising a input opening and two output opening which can be switched alternately, a feedback pipe connected to the input opening, a vaporization means and a water collection tank connected to above two output opening, respectively; wherein the vaporization means extended outside the box body with a circulation pipe and the water collection tank extended outside the box body with a gas outlet pipe; during its operation, feedback pipe and circulation pipe are connected to distal ends of conduit or closed space, the disinfecting gas generated by vaporization means is sent to conduit or closed space with the help of blower; after finishing disinfecting work, the gas in feedback pipe is filtered by water collection tank and the purified gas is discharged to atmosphere, therefore the automatic disinfecting means of present utility is not harmful to environment and can carry out disinfecting work with better effect than manual work.

It is another object of the present utility to provide an automatic disinfecting means for smoky gas in conduit or closed space with which the disinfecting work can be executed without needing workman entering the conduit or closed space, thus preventing workman from being infected and saving the manual work.

BRIEF DESCRIPTION OF THE DRAWING

In order to better understand the present utility, reference should be made to the following detailed description taken in junction with the accompanying drawings wherein.

BRIEF DESCRIPTION OF THE NUMERAL

| | |
|---|---|
| 10 box body | 20 blower |
| 21 input opening | 22 first output opening |
| 23 second output opening | 24 valve |
| 25 isolation mask | |
| 30 vaporization means | 31 gas outlet |
| 32 vapor generator | 40 water collection tank |
| 41 liquid | 42 gas outlet pipe |
| 43 drain pipe | 44 injection pipe |
| 45 filtering mesh | 50 feedback pipe |
| 51 filter | 60 circulation pipe |
| 61 T-pipe | 62 valve |
| 63 covering plate | 70 controlling box |
| 71 circuit | 72 sensor |
| 80 conduit | 90 closed space |

DETAILED DESCRIPTION OF THE UTILITY

Figure 1:
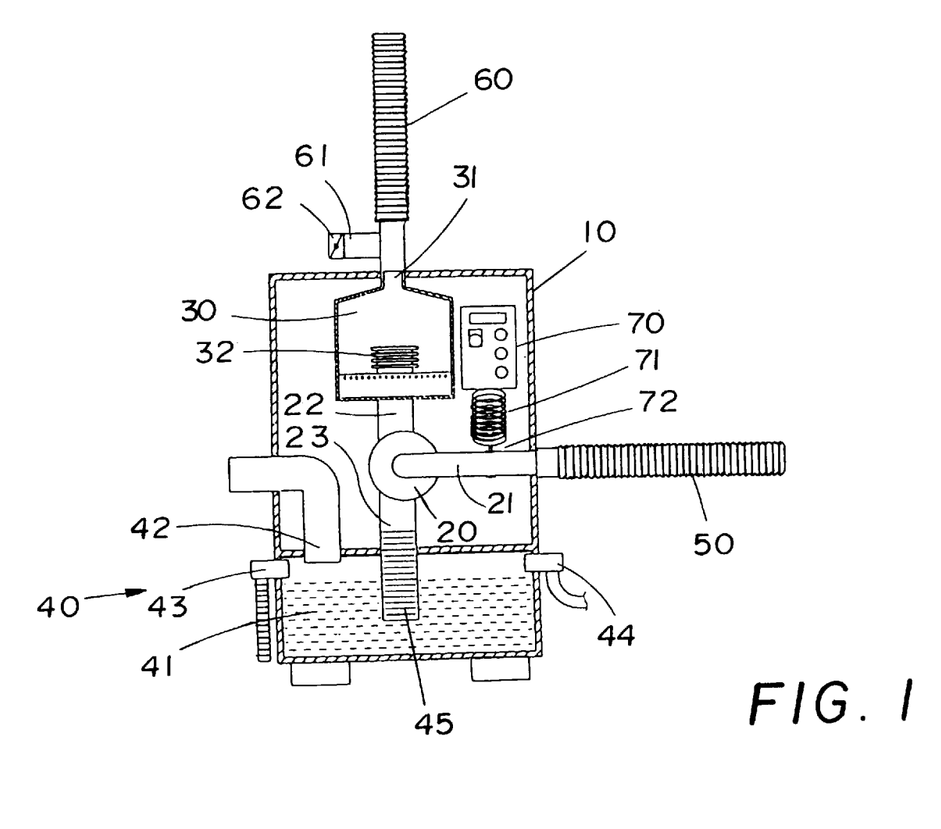
FIG. 1 is a schematic diagram of present utility.
Figure 2:
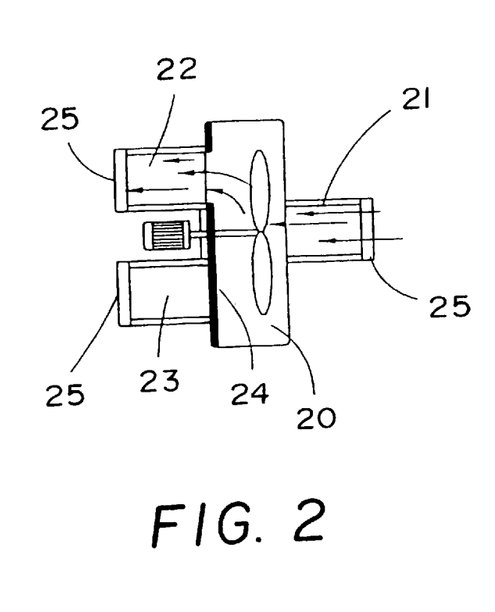
FIGS. 2 and 3 show the switching status of the outlet of blower in present utility.
Figure 3:
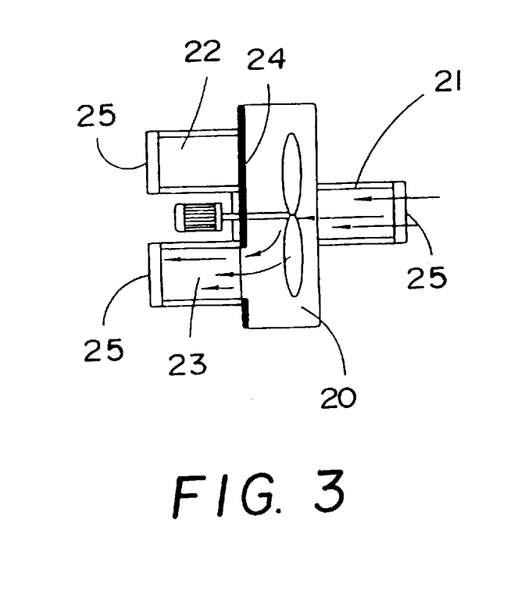

As shown in FIG. 1, the automatic disinfecting means for smoky gas in conduit or closed space comprising:

a box body 10 which is a closed space;

a blower 20 which is arranged within box body 10 and whose speed is variably controlled by a controlling box 70, the blower further comprising a input opening 21 and two output opening 22, 23 (hereinafter referred as first output opening 22 and second output opening 23), first output opening 22 and second output opening 23 being switched alternately by a valve 24 to discharge the gas input from input opening 21, and each of input opening 21, first output opening 22 and second output opening 23 being provided with isolation mask 25 at its ended portion to prevent dust-burst, referring again to FIG. 1, second output opening 23 being provided with filtering mesh 45 at its ended portion to filter out dust;

a vaporization means 30 with one end connected to first output opening 22 of blower 20 and another end having a gas outlet 31, wherein vaporization means 30 is provided with a vapor generator 32 to generate disinfecting gas after placing disinfecting medium within vaporization means 30, besides, the function of vapor generator 32 can be replaced by a canned disinfecting gas or direct-injecting of disinfecting gas;

a water collection tank 40 arranged within box body 10 and containing liquid 41 with depth larger than half the tank height, wherein the second output opening 23 of blower 20 dips into water collection tank 40 and is below the surface of liquid 41, the water collection tank 40 is provided with a gas outlet pipe 42 situated above the surface of liquid 41 and extending outwardly to discharge gas filtered by liquid 41, moreover, water collection tank 40 is provided with a drain pipe 43 which is lower than gas outlet pipe 42 and higher than surface of liquid 41 to drain excess liquid 41 and prevent liquid 41 from flowing from gas outlet pipe 42, and a water injection pipe 44 to exchange liquid 41;

a feedback pipe 50 which has flexibility and is connected to input opening 21 of blower 20 at its back end;

a circulation pipe 60 which has flexibility and whose front end is connected to gas outlet 31 of vaporization means 30 through a T-pipe 61, wherein T-pipe 61 has another outlet with a valve 62 to control the access of clean gas;

a controlling box 70 arranged on box body 10 or extended outside box body 10, which is functioned to control blower 20 and vaporization means 30 by wire or remotely and to control valve 62 of T-pipe 61, wherein a sensor 72 is extended from controlling box 70 through circuit 71 to input opening 21 of blower 20 to sense the content of disinfecting gas flowing through blower 20.

Figure 4:
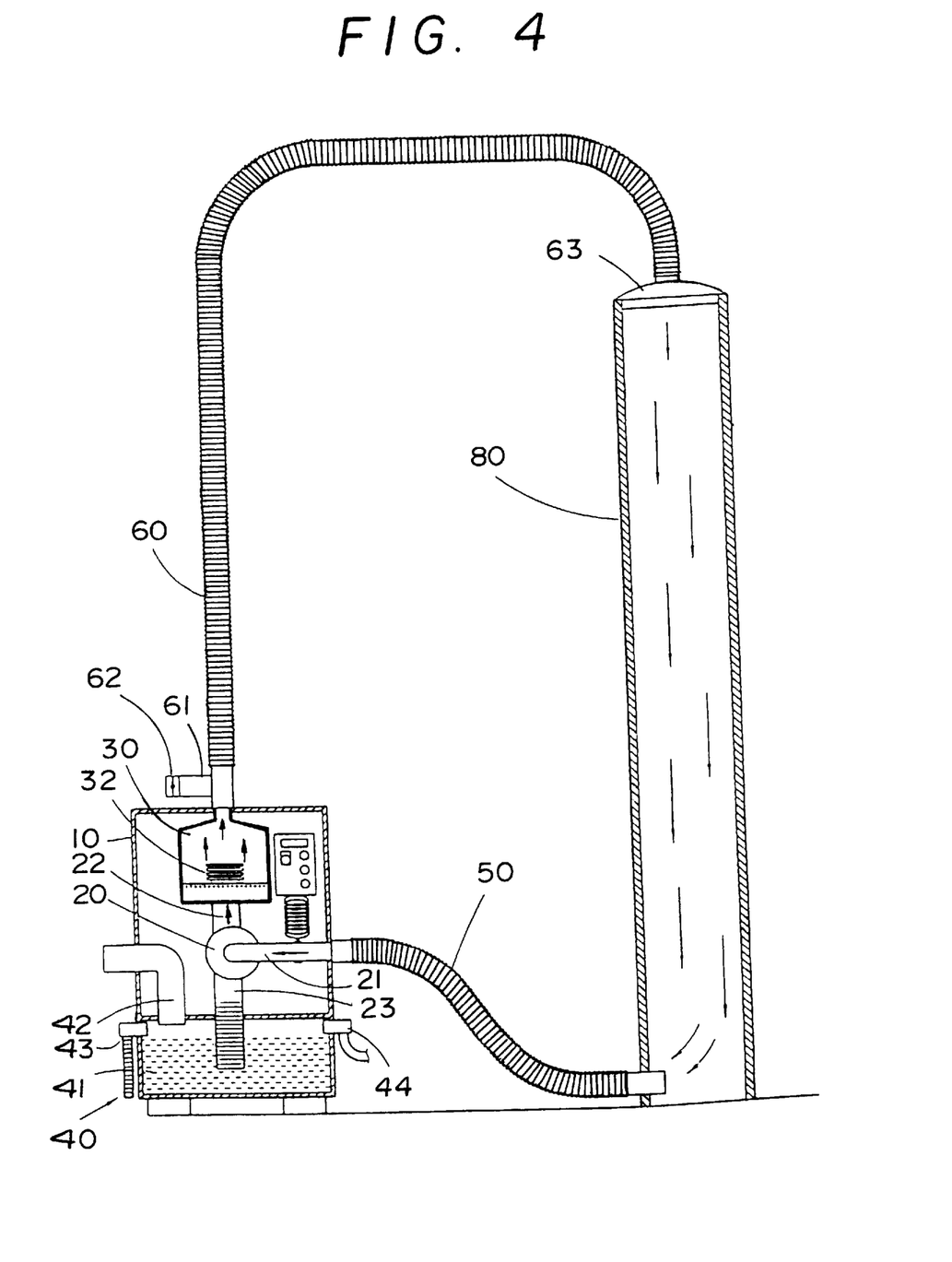
FIGS. 4 and 5 show the application of present utility in a conduit.
Figure 6:
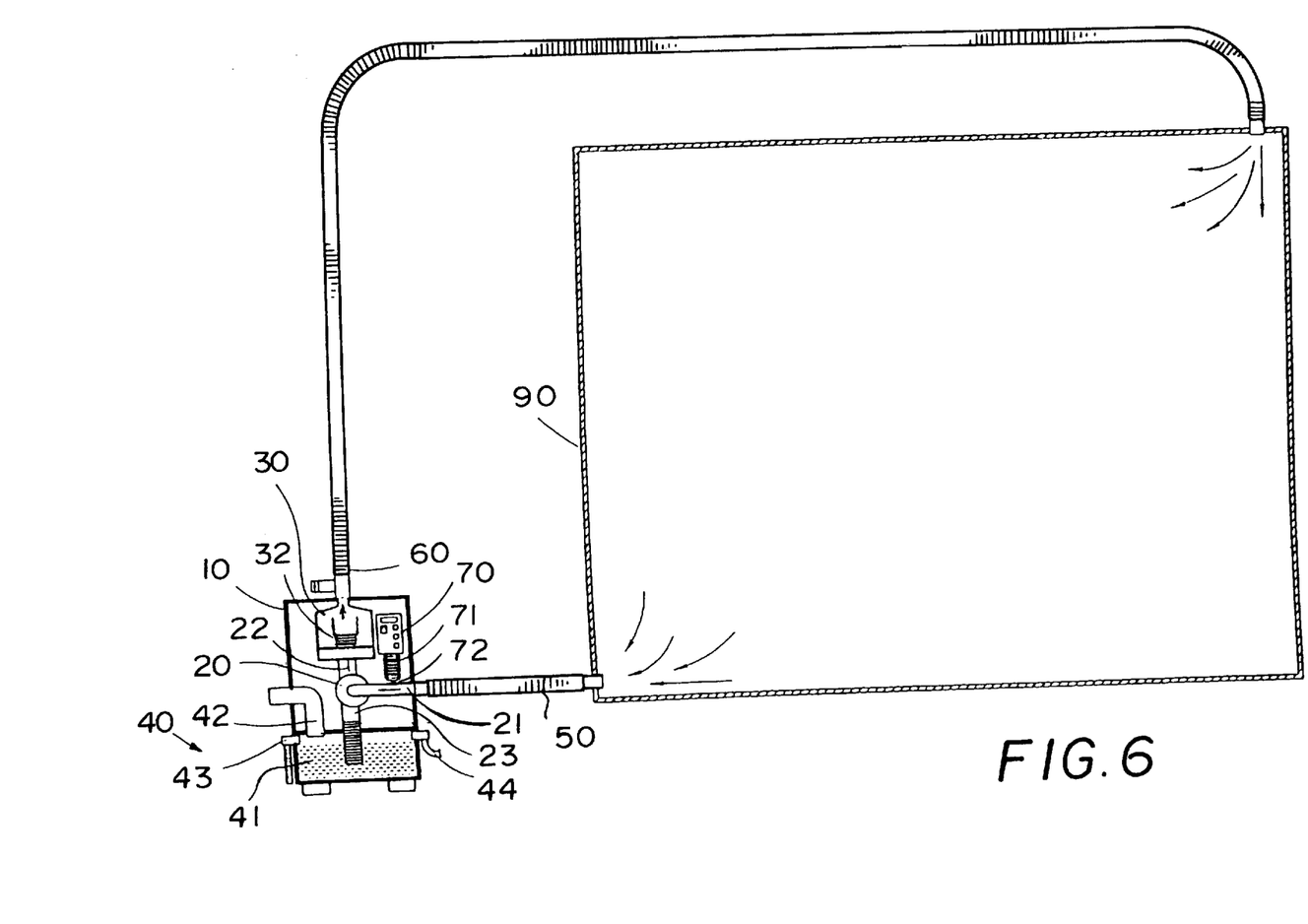
FIGS. 6 and 7 show the application of present utility in a closed space.

As shown in FIGS. 4 and 6, when present utility is applied in conduit and closed space, input opening 21 is opened by valve 24 of blower 20 and second output opening 23 is closed to form a passage between input opening 21 and first output opening 22. Besides, valve 62 of T-pipe 61 also need to be closed. The feedback pipe 50 and circulation pipe 60 are connected to the distal end of conduit 80 or closed space 90 respectively. The end portion connected to conduit 80 is provided with a covering plate 63 to close conduit 80. Meanwhile, controlling box 70 operates blower 20 and vaporization means 30 to generate disinfecting gas and the gas will flow into conduit 80 or closed space 90 through circulation pipe 60. Besides, feedback pipe 50 will generate a strong negative pressure due to the counter-flow in circulation pipe 60, thereby the gas in conduit 80 or closed space 90 can be distributed throughout to proceed disinfecting work. The controlling box 70 will stop vaporization means 30 if sensor 72 at input opening 21 of blower 20 detects that content of disinfecting gas has reached desired level. The disinfecting, work in conduit 80 or closed space 90 is finished after a predetermined period.

Figure 5:
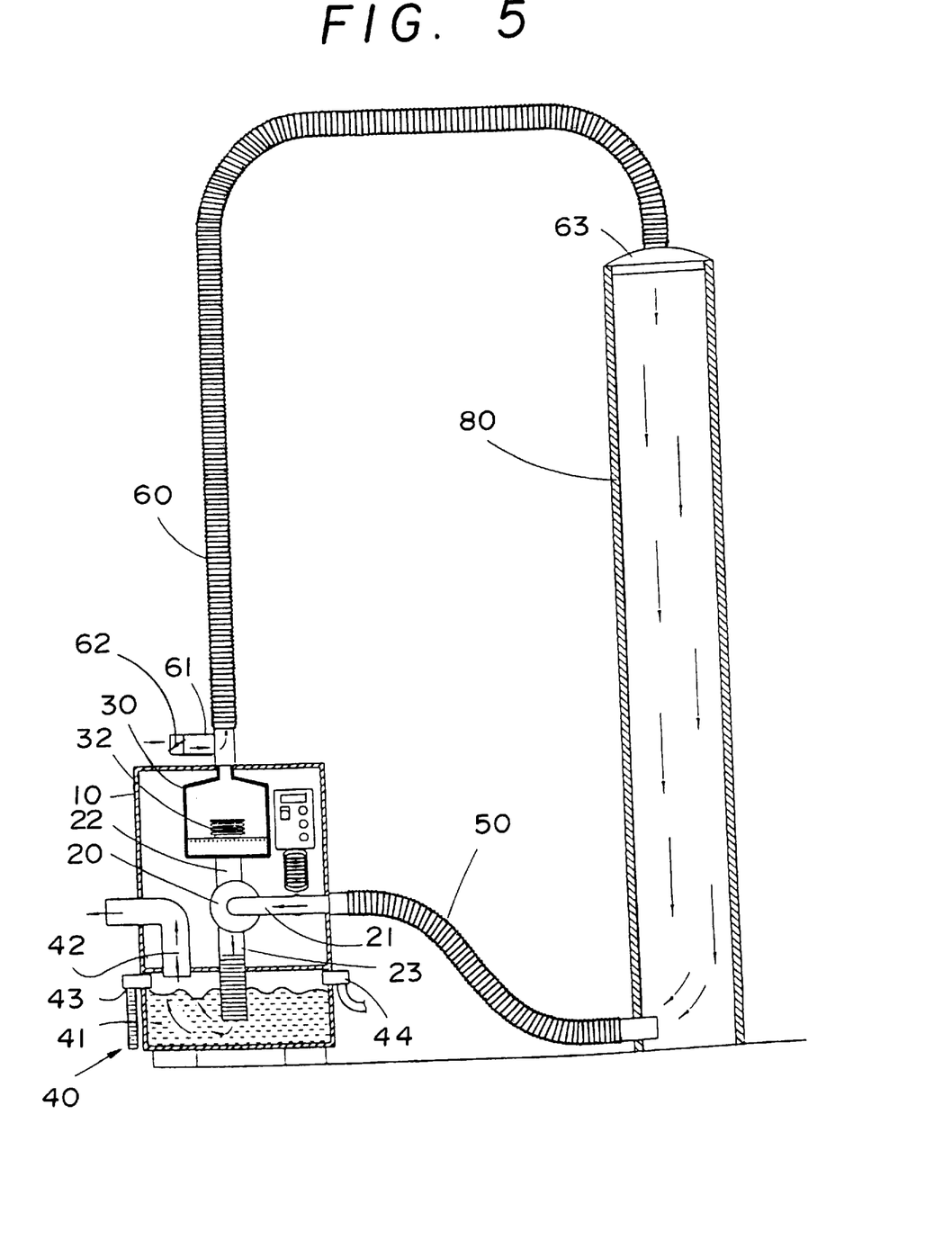
Figure 7:
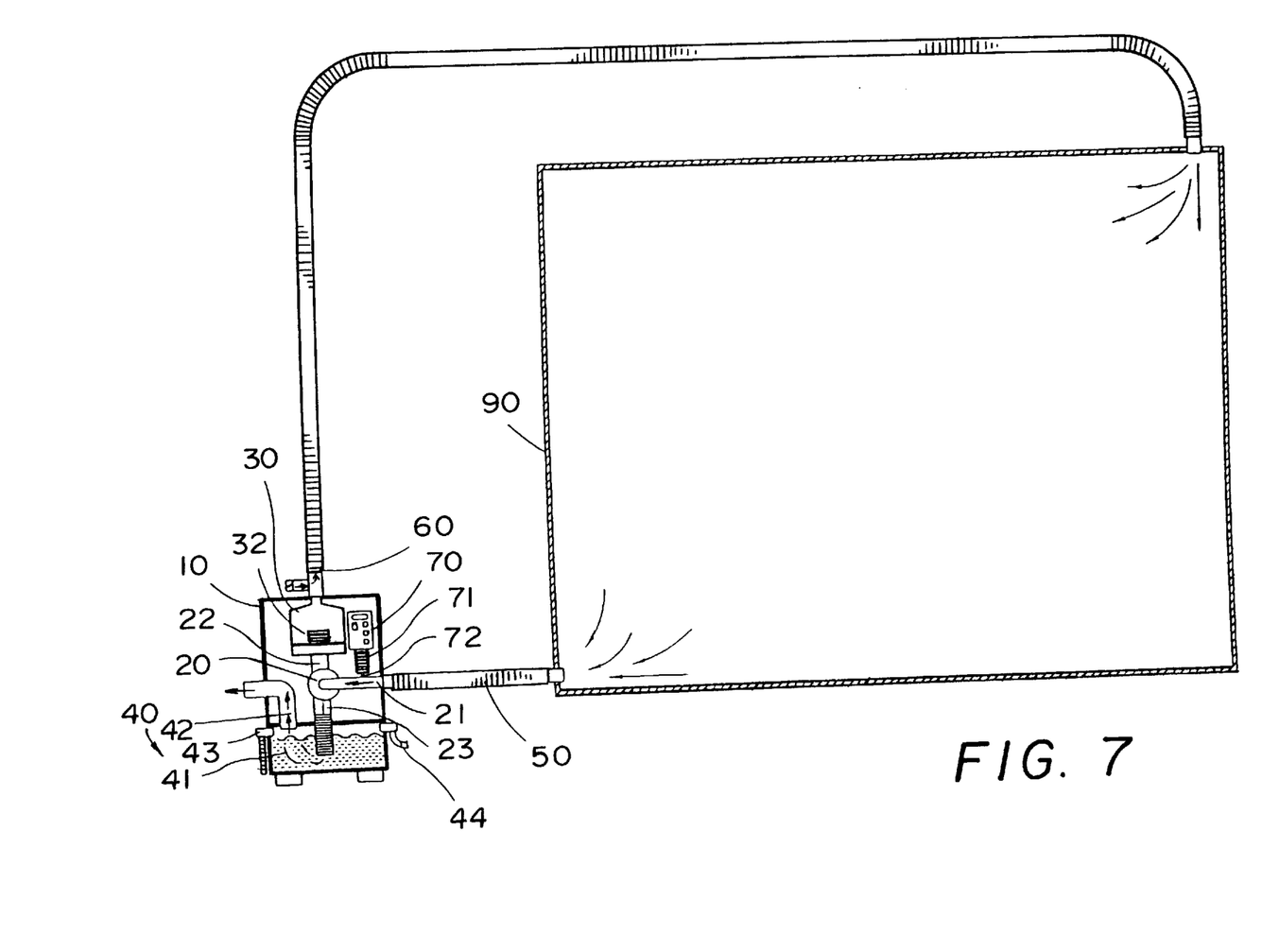

Moreover, as shown in FIGS. 5 and 7, there is still disinfecting gas remaining within conduit 80 or closed space 90 after the finish of disinfecting work. The controlling box 70 operates valve 24 to close first output opening 22 of blower 20 and the second output opening 23 is opened to make a passage with input opening 21. Besides, valve 62 of T-pipe 61 also need to be opened. The blower 20 is restarted to draw the gas containing disinfecting gas from conduit 80 or closed space 90 to water collection tank 40 through second output opening 23. Meanwhile, clean gas can be injected from T-pipe 61 to conduit 80 or closed space 90, and the gas containing disinfecting gas will be dissolved in liquid 41 of water collection tank 40. The chemical agent used to disinfecting and dust will remain on liquid 41, filter 51 or filtering mesh 45, and purified gas will discharge to atmosphere through gas outlet pipe 42. The controlling box 70 will stop blower 20 if sensor 72 at input opening 21 of blower 20 detects that content of discharged gas has reached desired level, thus finishing the disinfecting operation.

Besides, as the present utility is applied in closed space 90, according the size and shape of closed space 90, the circulation pipe 60 is branched to several sub-pipes which are connected to each corner to distribute disinfecting gas within closed space 90 uniformly.

Figure 8:
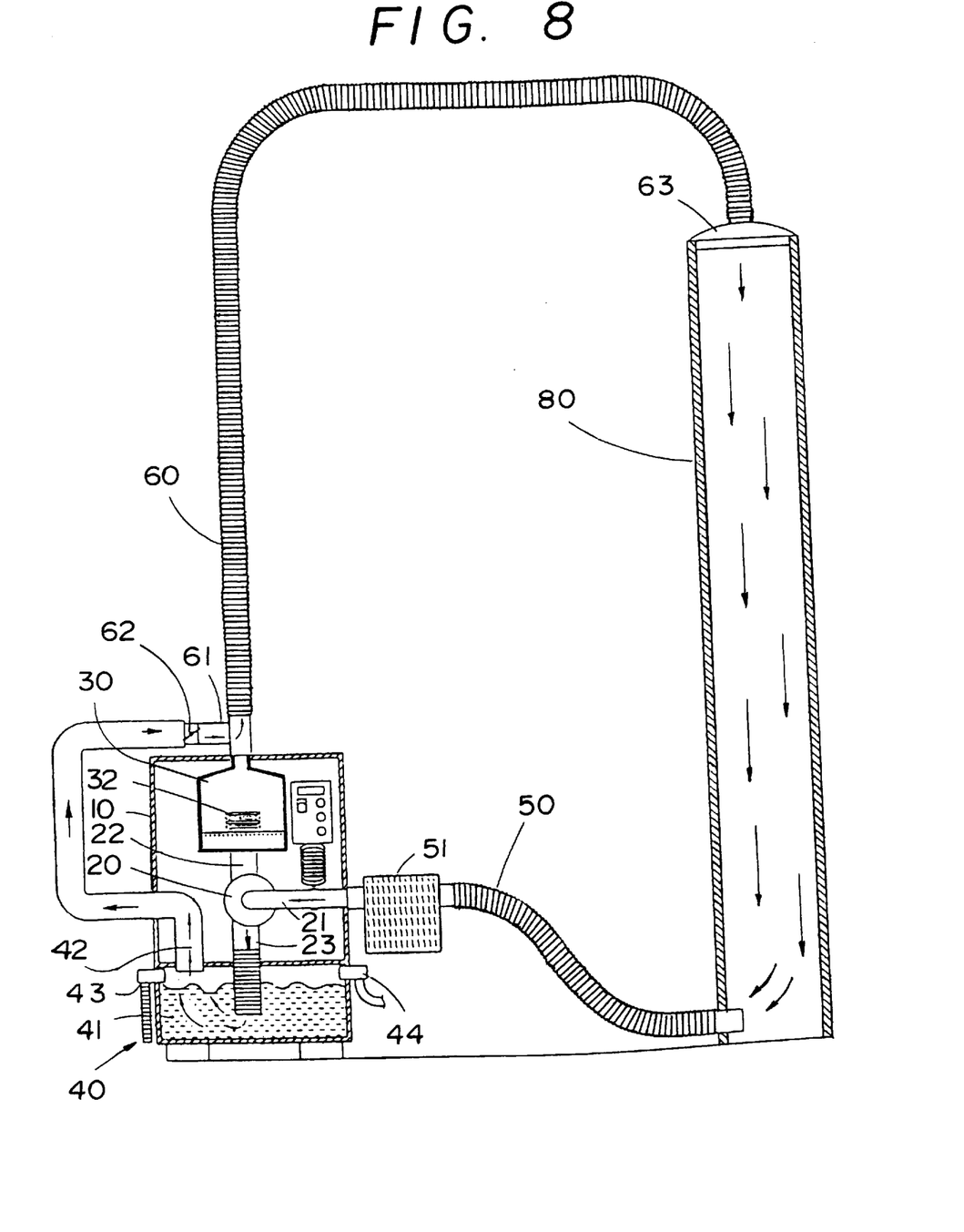
FIG. 8 shows another embodiment of present utility.

As shown in FIG. 8, the gas outlet pipe 42 of water collection tank 40 can be extended to connect to T-pipe 61 directly, thus connecting water collection tank 40 and circulation pipe 60. The purified gas filtered and collected by water collection tank 40 will be led to conduit 80 or closed space 90 through gas outlet pipe 42, T-pipe 61 and circulation pipe 60. Besides, when present utility is applied in situation of large and dense dust, a filter 51 should connected between back side of feedback pipe 50 and input opening 21 of blower 20 to enhance filtering efficiency.

As previously described, the present utility provides an automatic disinfecting means for smoky gas in conduit or closed space which is not harmful to environment and can carry out disinfecting work with better effect than manual work.

While the present utility has been described in connection with what is presently considered to be the most practical and preferred embodiments, it is to be understood that the invention is not limited to the disclosed embodiment, but, on the contrary, it is intended to cover various modification and equivalent arrangement included within the spirit and scope of the appended claims.

What is claimed is:

1. An automatic disinfecting means for smoky gas in conduit or closed space comprising:

a box body which is a closed space;

a blower which is arranged within said box body, wherein the blower comprise a input opening, a first output opening and a second output opening, first output opening and second output opening being switched alternately by a valve to discharge the gas input from said input opening;

a vaporization means with one end connected to said first output opening of said blower and another end having a gas outlet, wherein said vaporization means is provided with a vapor generator to generate disinfecting gas after placing disinfecting medium within said vaporization means;

a water collection tank arranged within said box body and containing liquid with depth larger than half the tank height, wherein said second output opening of said blower dips into said water collection tank and is below the surface of said liquid, said water collection tank is provided with a gas outlet pipe situated above the surface of said liquid and extending outwardly to discharge gas filtered by said liquid;

a feedback pipe which has flexibility and is connected to said input opening of said blower at its back end;

a circulation pipe which has flexibility and whose front end is connected to said gas outlet of said vaporization means through a T-pipe, wherein said T-pipe has another outlet with a valve;

a controlling box which is functioned to control said blower and said vaporization means, wherein a sensor is extended from said controlling box through circuit to said input opening of said blower to sense the content of disinfecting gas flowing through said blower;

for carrying out disinfecting work, the output of said blower is switched to said first output opening and the valve of said T-pipe is closed, said feedback pipe and said circulation pipe are connected to distal end of conduit or closed space, the disinfecting gas generated by said vaporization means is sent to conduit or closed space with the help of said blower; after finishing, disinfecting work, the output of said blower is switched to said second output opening and the valve of said T-pipe is opened, the gas in said feedback pipe is filtered by said water collection tank and the purified gas is discharged to atmosphere.

2. An automatic disinfecting means for smoky gas in conduit or closed space as in claim 1, wherein the function of said vapor generator can be replaced by a canister of disinfecting gas or direct-injecting of disinfecting gas.

3. An automatic disinfecting means for smoky gas in conduit or closed space as in claim 1, wherein said water collection tank is provided with a drain pipe which is lower than said gas outlet pipe and higher than surface of said liquid to drain excess liquid and prevent said liquid from flowing from said gas outlet pipe, and a water injecting pipe to exchange said liquid.

4. An automatic disinfecting means for smoky gas in conduit or closed space as in claim 1, wherein one end of said second output opening of said blower has filtering mesh and is dipped into said liquid of said water collection tank.

5. An automatic disinfecting means for smoky gas in conduit or closed space as in claim 1, wherein a filter is connected between back side of said feedback pipe and said input opening of said blower.

6. An automatic disinfecting means for smoky gas in conduit or closed space as in claim 1, wherein the speed of said blower can be controlled by said controlling box.

7. An automatic disinfecting means for smoky gas in conduit or closed space as in claim 1, wherein said gas outlet pipe of said water collection tank can be extended to and connected directly to said T-pipe, thus being connected to said circulation pipe.

8. An automatic disinfecting means for smoky gas in conduit or closed space as in claim 1, wherein each of said input opening, first output opening and second output opening of said blower is provided with a isolation mask at its ended portion to prevent dust-burst.

\* \* \* \* \*